(12) United States Patent
Klein et al.

(10) Patent No.: US 11,079,366 B2
(45) Date of Patent: Aug. 3, 2021

(54) PLUME CHARACTERIZATION USING SYNCHRONIZED MEASUREMENTS OF GAS COMPOSITION, WIND DIRECTION, AND WIND SPEED

(71) Applicant: International Business Machines Corporation, Armonk, NY (US)

(72) Inventors: Levente Klein, Tuckahoe, NY (US); Theodore van Kessel, Millbrook, NY (US); Ramachandran Muralidhar, Mahopac, NY (US); Michael A. Schappert, Wappingers Falls, NY (US)

(73) Assignee: INTERNATIONAL BUSINESS MACHINES CORPORATION, Armonk, NY (US)

( * ) Notice: Subject to any disclaimer, the term of this patent is extended or adjusted under 35 U.S.C. 154(b) by 384 days.

(21) Appl. No.: 15/923,118

(22) Filed: Mar. 16, 2018

(65) Prior Publication Data
US 2019/0285600 A1    Sep. 19, 2019

(51) Int. Cl.
*G01N 33/00* (2006.01)
*G01M 3/04* (2006.01)
(Continued)

(52) U.S. Cl.
CPC ........... *G01N 33/0073* (2013.01); *G01M 3/04* (2013.01); *G01M 3/38* (2013.01); *G01N 1/2273* (2013.01); *G01N 2033/0068* (2013.01)

(58) Field of Classification Search
CPC ...... G01N 33/0073; G01N 2033/0068; G01M 3/26; G01M 3/22
See application file for complete search history.

(56) References Cited

U.S. PATENT DOCUMENTS

| 5,604,299 A | 2/1997 | Cobb | |
|---|---|---|---|
| 2011/0109464 A1* | 5/2011 | Lepley | G01N 33/0075 340/605 |

(Continued)

FOREIGN PATENT DOCUMENTS

EP    0448360 A1    9/1991

OTHER PUBLICATIONS

Bhattacharyya et al., "Fast response methane sensor using nanocrystalline zinc oxide thin films derived by sol-gel method" Sensors and Actuators B: Chemical 124.1, 2007, pp. 62-67.
(Continued)

*Primary Examiner* — Nimeshkumar D Patel
*Assistant Examiner* — Gedeon M Kidanu
(74) *Attorney, Agent, or Firm* — Cantor Colburn LLP; Anthony Curro

(57) ABSTRACT

Embodiments of the invention are directed to an integrated sensing system that includes a movable orientation device configured to dynamically position the movable orientation device based on receiving an air-flow. A gas sensor is coupled to the movable orientation device. The gas sensor includes a recognition element configured to detect a chemical in a plume. The movable orientation device is configured to perform a synchronized sensing operation that includes, based at least in part on the movable orientation device receiving the air-flow, moving the movable orientation device to dynamically maintain a predetermined orientation of the movable orientation device relative to a direction of the air-flow. The predetermined orientation includes positioning the gas sensor in a path of the air-flow, wherein the air-flow is influencing the plume to move along the path such that the recognition element is exposed to the plume.

10 Claims, 11 Drawing Sheets

(51) Int. Cl.
*G01M 3/38* (2006.01)
*G01N 1/22* (2006.01)

(56) References Cited

U.S. PATENT DOCUMENTS

| | | | |
|---|---|---|---|
| 2011/0213554 A1* | 9/2011 | Archibald | G01V 9/007 |
| | | | 702/6 |
| 2014/0002639 A1* | 1/2014 | Cheben | G08B 21/14 |
| | | | 348/135 |
| 2015/0185194 A1 | 7/2015 | Prince et al. | |
| 2017/0016866 A1 | 1/2017 | Chey et al. | |
| 2017/0097274 A1* | 4/2017 | Thorpe | G01M 3/38 |
| 2017/0241936 A1 | 8/2017 | Chang et al. | |
| 2018/0120278 A1* | 5/2018 | Hoorfar | G01N 33/497 |
| 2018/0127093 A1* | 5/2018 | Christensen | G01P 5/02 |
| 2018/0188129 A1* | 7/2018 | Choudhury | G01M 3/38 |
| 2019/0156600 A1* | 5/2019 | Potyrailo | B61C 17/08 |
| 2020/0033157 A1* | 1/2020 | Kaufman | B64D 1/16 |

OTHER PUBLICATIONS

De Angelis et al., "Selectivity and stability of a tin dioxide sensor for methane," Sensors and Actuators B: Chemical 28.1, 1995, pp. 25-29.

Figaro USA Inc., "Technical Information for Methane Gas Sensors," http://www.figarosensor.com/products/2611Dtl.pdf. (retrieved Jan. 3, 2018), 13 pages.

Lu et al., "Wind Sensor for Miniature Robot Chemical Plume Tracking," IEEE International Conference on Robotics and Biomimetics, 2007, 6 pages.

Quaranta et al., "A novel gas sensor based on SnO2/Os thin film for the detection of methane at low temperature," Sensors and Actuators B: Chemical 58, 1999, pp. 350-355.

Russell et al., "A novel airflow sensor for miniature mobile robots," Mechatronics 10.8, 2000, pp. 935-942.

Synkera Technologies, Inc., "UltraKera TO Methane Sensor P/N 729," http://www.synkerainc.com/online-store/product/149-ultrakera-to-methane-sensor (retrieved Jan. 3, 2018), 2 pages.

Tan et al., "Development of an Optical Gas Leak Sensor for Detecting Ethylene, Dimethyl Ether and Methane," Sensors 13.4, 2013, pp. 4157-4169.

Tillman et al., "Mid-infrared absorption spectroscopy of methane using a broadband femtosecond optical parametric oscillator based on aperiodically poled lithium niobate," Journal of Optics A: Pure and Applied Optics 7.6, 2005, pp. S408-S414.

* cited by examiner

| | SYNCHRONIZED CAPTURE/STORAGE -A | SYNCHRONIZED CAPTURE/STORAGE -B | SYNCHRONIZED CAPTURE/STORAGE -C | SYNCHRONIZED CAPTURE/STORAGE -D |
|---|---|---|---|---|
| GAS SENSOR | METHANE 20% | METHANE 24% | METHANE 28% | METHANE 21% |
| WIND DIRECTION SENSOR | EAST | NORTHEAST | WEST | SOUTH |
| WIND SPEED SENSOR (mph) | 4mph | 1mph | 2mph | 3mph |
| GAS SENSOR LOCATION | GPS COORDIN. | GPS COORDIN. | GPS COORDIN. | GPS COORDIN. |
| TIME STAMPS | TIME STAMP DATA | TIME STAMP DATA | TIME STAMP DATA | TIME STAMP DATA |

FIG. 4

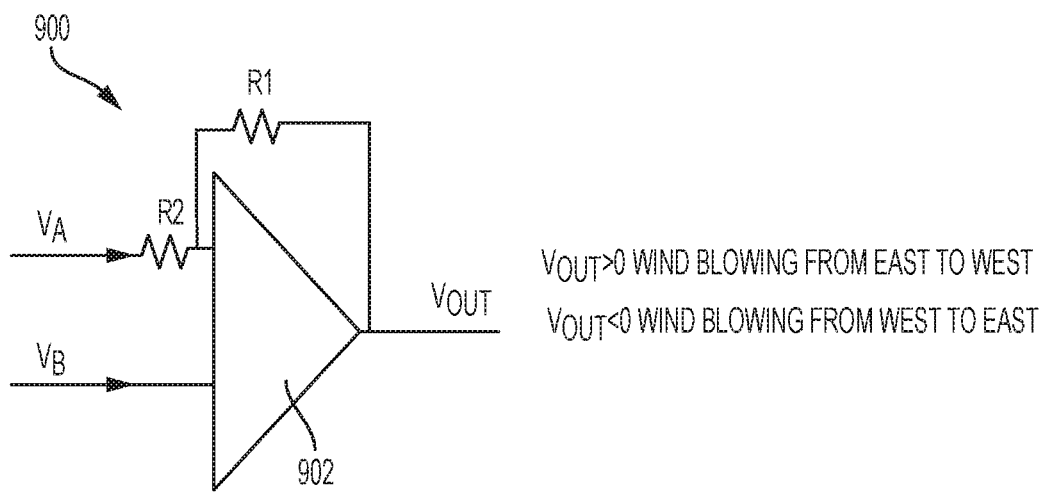
FIG. 9
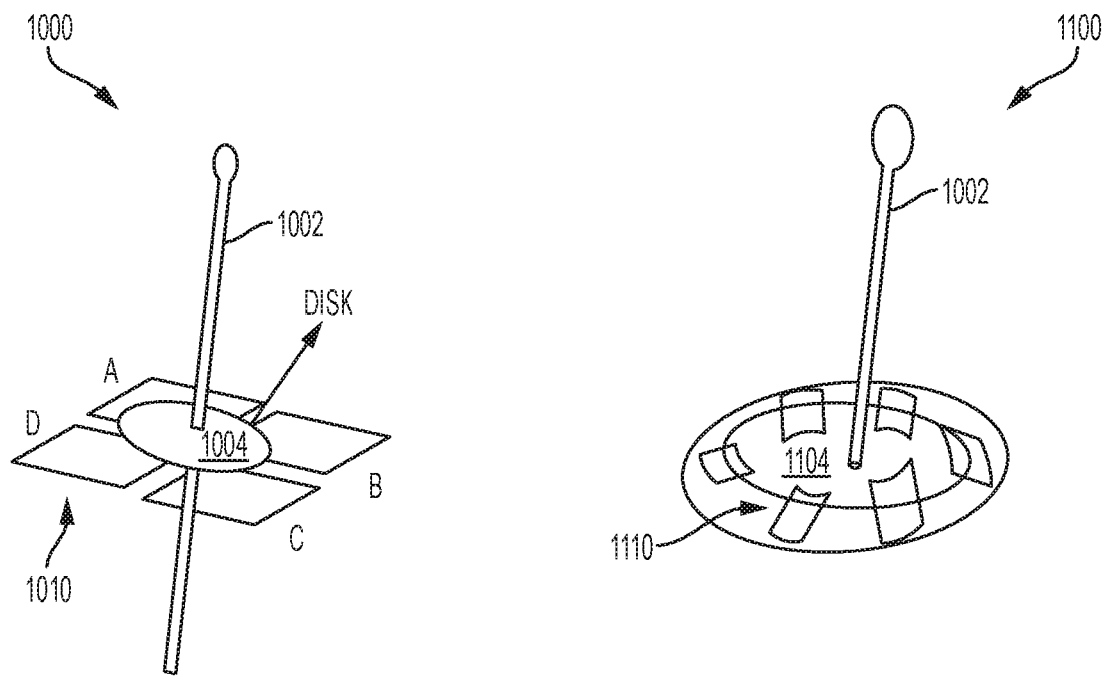
FIG. 10
FIG. 11

PLUME CHARACTERIZATION USING SYNCHRONIZED MEASUREMENTS OF GAS COMPOSITION, WIND DIRECTION, AND WIND SPEED

STATEMENT REGARDING FEDERALLY SPONSORED RESEARCH OR DEVELOPMENT

This invention was made with Government support under DE-AR0000540 awarded by Advanced Research Development Agency. The Government has certain rights to this invention.

BACKGROUND

The present invention relates generally to plume characterization systems. More specifically, the present invention relates to sensor-based plume characterization systems and methods for estimating the location of a gas leak from a gas source based at least in part on the synchronized measurement of gas composition, wind direction, and/or wind speed.

In hydrodynamics, a plume is a column of one fluid moving through another. Several effects control the motion of the fluid, including momentum (inertia), diffusion and buoyancy (density differences). As a plume moves away from its source, it can widen because of entrainment of the surrounding fluid at its edges. Plume shapes and travel paths can be influenced by flow in the ambient fluid, for example, if a local air-flow (e.g., a wind current) impacts the plume and carries it in a particular direction. Plume characterization systems have been developed that utilize a sensor network, data analysis, and prediction algorithms to monitor the dispersion of a plume containing an airborne contaminant, as well as estimate the location of the source of the contaminant.

SUMMARY

Embodiments of the invention are directed to an integrated sensing system that includes a movable orientation device configured to dynamically position the movable orientation device based on receiving an air-flow. A gas sensor is coupled to the movable orientation device. The gas sensor includes a recognition element configured to detect a chemical in a plume. The movable orientation device is configured to perform a synchronized sensing operation that includes, based at least in part on the movable orientation device receiving the air-flow, moving the movable orientation device to dynamically maintain a predetermined orientation of the movable orientation device relative to a direction of the air-flow. The predetermined orientation includes positioning the gas sensor in a path of the air-flow, wherein the air-flow is influencing the plume to move along the path such that the recognition element, when positioned in the path by the movable orientation device, is exposed to the plume.

Embodiments of the invention are directed to an integrated sensing system that includes a wind vane configured to move around a pivot. A gas sensor is coupled to the wind vane, wherein the gas sensor includes a chemi-sensing element configured to detect a chemical in a plume. The system further includes a wind speed sensor and a wind direction sensor, wherein the integrated sensing system is configured to perform a synchronized sensing operation that includes, based at least in part on the wind vane detecting the direction of a wind current that is influencing the plume to move in a path, using the wind vane to dynamically position the gas sensor relative to the path such that the recognition element is in the path and exposed to the plume; detecting, using the wind speed sensor, a speed of the wind current that is influencing the plume to move in the path; and detecting, using the wind direction sensor, the direction of the wind current that is influencing the plume to move in the path. In some embodiments of the invention, the system is configured to calculate a wind speed and a wind direction. In some embodiments of the invention, the synchronized sensing operation further includes detecting, using the gas sensor and chemi-sensing element, the instantaneous chemical composition of the plume.

Embodiments of the invention are directed to a method of estimating a location of a fluid leak from a source. The method includes providing a first gas sensor configured to detect a chemical in a plume, wherein an air-flow impacts and carries the plume to the first gas sensor. A first air-flow direction sensor is provided, wherein the first air-flow direction sensor is configured to detect a direction of the air-flow that impacts and carries the plume to the first gas sensor. Based at least in part on a determination that a first gas composition output from the first gas sensor exceeds a first threshold, a processor is used to implement a synchronized sensor reading operation that includes reading a first air-flow direction output from the first air-flow direction sensor, wherein the first air-flow direction output comprises a first direction of the air-flow that impacts and carries the plume to the first gas sensor; and storing sensed data in a relational database. The sensed data includes the first air-flow direction output and the first gas composition output. The processor is used to access from the relational database the first air-flow direction output and the first gas composition output; and execute a process to estimate the location of the fluid leak, wherein the process to estimate the location of the fluid leak includes analyzing the first air-flow direction output and the first gas composition output. In some embodiments of the invention, a network of sensors is provided by including at least a second gas sensor and a second air-flow direction sensor, configured and arranged in substantially the same manner as the first gas sensor and the first air-flow direction sensor. In some embodiments of the invention, the various sensors are positioned in relatively close proximity to one another. In some embodiments of the invention, the processor is used to also access from the relational database a second air-flow direction output from the second air-flow direction sensor and a second gas composition output for the second gas sensor in order to execute the process to estimate the location of the fluid leak. In some embodiments of the invention, the process to estimate the location of the fluid leak includes analyzing the intersection of the first air-flow direction output of the first air-flow direction sensor with the second air-flow direction output of second air-flow direction sensor, along with analyzing the intersection of the first gas composition output of first gas sensor and the second gas composition output of the second gas sensor.

Additional features and advantages are realized through the techniques described herein. Other embodiments and aspects are described in detail herein. For a better understanding, refer to the description and to the drawings.

BRIEF DESCRIPTION OF THE DRAWINGS

The subject matter which is regarded as the present invention is particularly pointed out and distinctly claimed in the claims at the conclusion of the specification. The foregoing and other features and advantages are apparent from the following detailed description taken in conjunction with the accompanying drawings in which:

FIG. 4 depicts a table illustrating an example of a relational database according to embodiments of the invention;

FIG. 9 depicts a schematic diagram of a portion of a plume characterization system according to embodiments of the invention;

FIG. 10 depicts a schematic diagram of a portion of a plume characterization system according to embodiments of the invention;

FIG. 11 depicts a schematic diagram of a portion of a plume characterization system according to embodiments of the invention;

Figure 1:
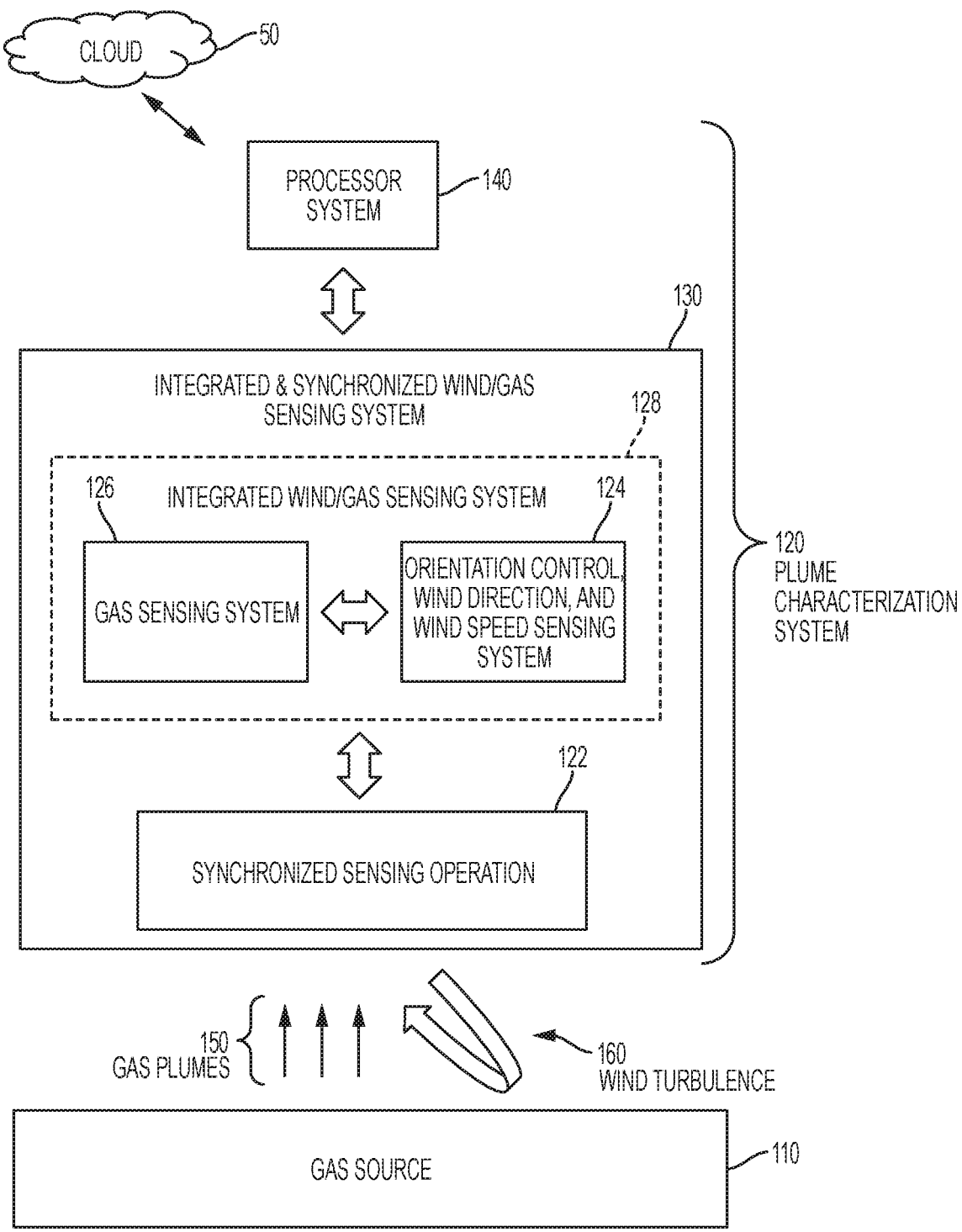
FIG. 1 depicts a block diagram of a plume characterization system according to embodiments of the invention.

In the accompanying figures and following detailed description of the disclosed embodiments, the various elements illustrated in the figures are provided with three or four digit reference numbers. The leftmost digit(s) of each reference number corresponds to the figure in which its element is first illustrated.

DETAILED DESCRIPTION

Various embodiments of the invention are described herein with reference to the related drawings. Alternative embodiments of the invention can be devised without departing from the scope of this invention. Various connections and positional relationships (e.g., over, below, adjacent, etc.) are set forth between elements in the following description and in the drawings. These connections and/or positional relationships, unless specified otherwise, can be direct or indirect, and the present invention is not intended to be limiting in this respect. Accordingly, a coupling of entities can refer to either a direct or an indirect coupling, and a positional relationship between entities can be a direct or indirect positional relationship. Moreover, the various tasks and process steps described herein can be incorporated into a more comprehensive procedure or process having additional steps or functionality not described in detail herein.

For the sake of brevity, conventional techniques related to semiconductor device and integrated circuit (IC) fabrication may or may not be described in detail herein. Moreover, the various tasks and process steps described herein can be incorporated into a more comprehensive procedure or process having additional steps or functionality not described in detail herein. In particular, various steps in the manufacture of semiconductor devices and semiconductor-based ICs are well known and so, in the interest of brevity, many conventional steps will only be mentioned briefly herein or will be omitted entirely without providing the well-known process details.

Turning now to a description of technologies that are more specifically relevant to the present invention, as previously noted herein, a plume is a column of one fluid moving through another. As a plume moves away from its source, the plume's shape and travel path can be influenced by flow in the ambient fluid, for example, if a local air-flow (e.g., a wind current) impacts the plume and carries it in a particular direction along a particular path.

Plume characterization systems have been developed that utilize a sensor network, data analysis algorithms, and prediction algorithms to monitor the dispersion of a plume containing an airborne contaminant, as well as estimate the location of the source of the contaminant. In some environments, the local air-flow is turbulent, which can require the plume characterization system to provide additional structures and computing power to account for the turbulent air-flow dynamically varying the plume's direction in space and time. Known plume characterization systems attempt to address the complications introduced by turbulent air-flow in the measuring environment by including wind direction and wind speed sensors in its sensor network; locating the sensor network further from potential sources of the leak in order to model data with known models such as a Gaussian plume model; acquiring the data across a large time interval where statistically enough data point are acquired to create an ordered distribution of measurement points; and providing more complex data analysis algorithms and prediction algorithms.

Turning now to an overview of aspects of the present invention, embodiments of the invention provide systems and methods to measure the chemical composition of a plume in close proximity of the source. If the leak is small (e.g., the amount of escaped gas is a few liter/minute) the plume is easily dispersed by wind as wispy plumes (i.e., lacking clarity and/or distinctness) that are hard to model using traditional plume dispersion models. For wispy plumes measured in close proximity of the source, the instantaneous wind direction and orientation has a direct impact on the plume shapes and location. Embodiments of the invention provide local wind direction and/or wind speed measurements that are synchronized (spatially, temporally, and/or logically) with chemical sensor measurements. In embodiments of the invention, the synchronization is triggered by providing an orientation device/mechanism that ensures that the chemical sensors are dynamically positioned and repositioned such that they face the direction in which the wind that is carrying the plume to the chemical sensor is blowing. In embodiments of the invention, the data acquisition frequency is triggered by the rate of change in chemical plume concentration and/or the wind direction change. For example, if the chemical plume concentration is increasing, the data acquisition rate is increasing. Similarly, if the chemical plume concentration is decreasing, the data acquisition frequency will decrease. With an integrated and synchronized sensing system in accordance with embodiments of the invention, both the plume concentration and the direction of the wind that carries the plum concentration can be captured with one system.

Embodiments of the chemical detection system described herein can be used to take substantially simultaneous measurement of the wind direction and a chemical reading from point sensors. The point sensors can be part of (e.g., a node) a wireless sensor network, wherein sensors are distributed across a certain area. In embodiments of the invention, each node integrates synchronized plume characterization and wind direction (and/or wind speed) measurements in a single integrated device or a single integrated housing. The sensor network can be configured to collect data from all sensing points and send the data to a cloud computing system. Alternatively, the signal can be processed at the point of acquisitions and just the integrated values are sent to the cloud in order to not overwhelm the available communications bandwidth. The measurement of chemical detection events can be used to quantify the leak rate and potential location of the leak based at least in part on data aggregation from the multiple sensors of the sensor network. Signals from the sensor can warn an operator about malfunctioning equipment on the well pad that has a leak. The signal can also be a warning sent to people carrying out maintenance work on the well pad to avoid areas that may or may not have chemical concentrations above predetermined limits. The signal from the sensor can automatically trigger a work order to initiate repair work. Based on the detected size of the leak, the signal can trigger the dispatch of a repairing crew immediately if it is determined that the leak is large and potentially more dangerous than a smaller leak.

Turning now to a more detailed description of aspects of the present invention, FIG. 1 depicts a block diagram of a plume characterization system 100 according to embodiments of the invention. The plume characterization system 120 is positioned to receive from a gas source 110 gas plumes 150 that are being directed by wind turbulence 160 from the gas source 110 along various paths, in various directions, and at various speeds. In embodiments of the invention, the plume characterization system 120 includes an integrated & synchronized wind/gas sensing system 130 communicatively coupled to a processor 140. In some embodiments of the invention, the plume characterization system 120 is communicatively coupled to a separate cloud computing system 50. In some embodiments of the invention, the cloud computing system 50 can be treated as an integral part of the plume characterization system 120. In embodiments of the invention, the integrated & synchronized wind/gas sensing system 130, which includes an integrated wind/gas sensing system 128. In embodiments of the invention, the integrated wind/gas sensing system 128 includes a gas sensing system 126 and an orientation control, wind direction sensing, and wind speed sensing system 124. In embodiments of the invention, the integrated wind/gas sensing system 128 is configured to perform a synchronized sensing operation 122. In some embodiments of the invention, aspects of the synchronized sensing operation 122 can be assisted and/or controlled using the processor system 140 and/or the cloud computing system 50.

Cloud computing system 50 is in wired or wireless electronic communication with one or all of the components of the plume characterization system 120. Cloud computing system 50 can supplement, support or replace some or all of the functionality of the components of the plume characterization system 120. Additionally, some or all of the functionality of the components of the plume characterization system 120 can be implemented as a node 10 (shown in FIG. 12) of the cloud computing system 50.

Figure 2:
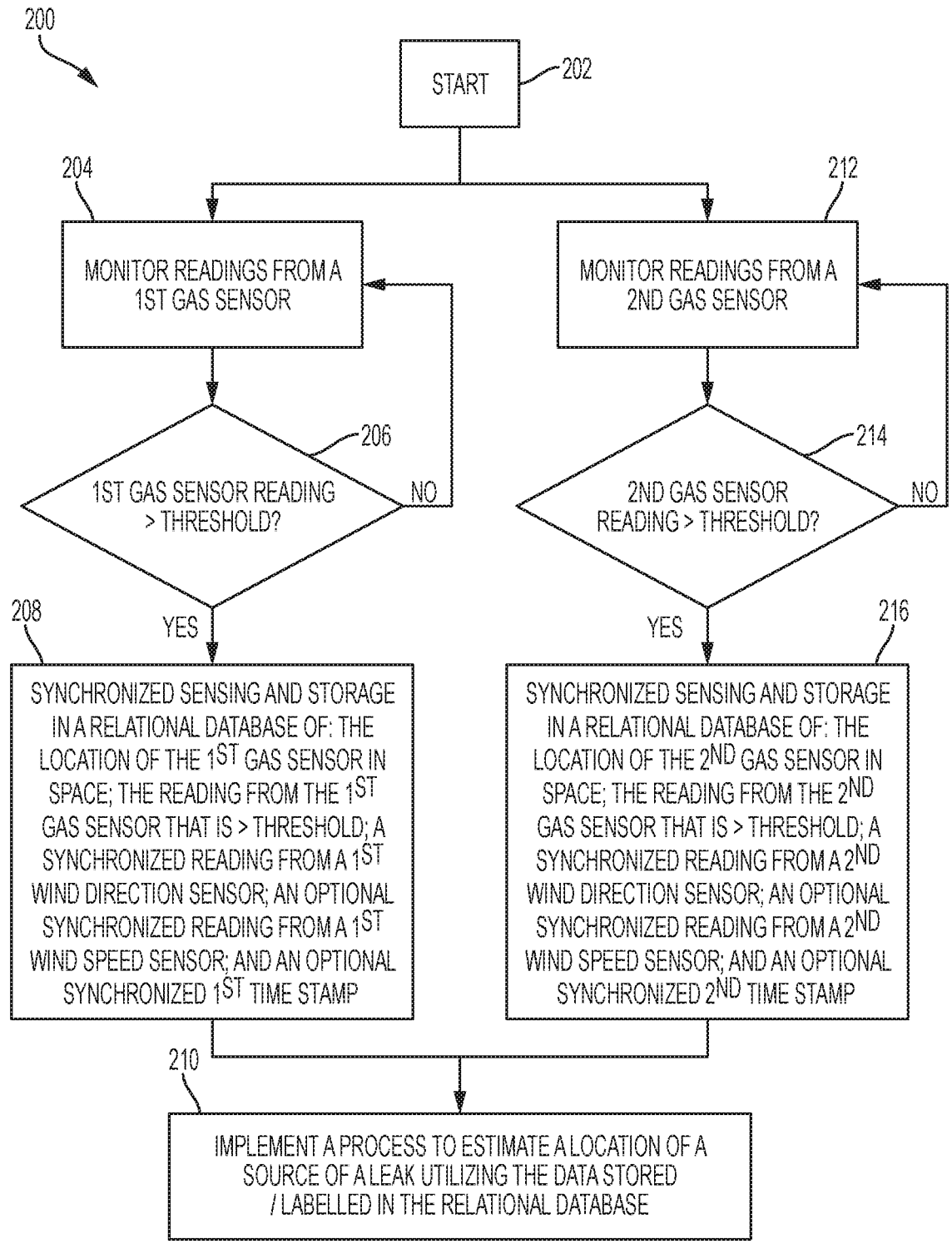
FIG. 2 depicts a flow diagram illustrating a methodology according to embodiments of the invention.

An exemplary operation of the plume characterization system 120 will now be described with reference to the methodology 200 illustrated by the flow diagram shown in FIG. 2, along with selected references to the plume characterization system 120 shown in FIG. 1. The methodology 200 corresponds to the synchronized sensing operation 122 (shown in FIG. 1), which is carried out by the integrated wind/gas sensing system 128, the processor 140 and the cloud computing system 50. The methodology 200 starts at block 202 and branches along two parallel paths. For ease of illustration and explanation, the methodology 200 is depicted for two parallel paths involving two separately located sensor sets, each of which includes a gas sensor, a wind direction sensor, and an optional wind speed sensor. It is understood that embodiments of the invention contemplate providing any number of sensor sets, including, for example, a single sensor set or multiple sensor sets.

In block 204, the processor 140 is used to monitor readings from a first gas sensor. In embodiments of the invention, the reading are the output data from the first gas sensor that represents the gas concentration currently being sensed by the first gas sensor. In embodiments of the invention, the first gas sensor can be implemented as a so-called "chemi-sensor" in which a semiconductor transistor acts as a transducer separated by an insulator layer (e.g. $SiO_2$) from a chemical recognition element that is selective to the target molecule (i.e., the analyte). Once the target molecule(s) bind to the recognition element, the charge distribution at the surface changes causing a corresponding change in the electrostatic surface potential at a gate of the semiconductor transistor. This change in the surface potential of the semiconductor acts like a gate voltage would in a traditional metal oxide semiconductor field effect transistor (MOSFET) by changing the amount of current that can flow between the source and drain electrodes of the transistor. This change in current (or conductance) can be measured and analyzed to detect the binding of the analyte to the chemical recognition element. In embodiments of the invention, the gas sensor can be an "optical-sensor" that detects light absorption by the chemical plume that contains one of the chemical gases. The light source in this case can be a laser light that is finely tuned to a wavelength that triggers the molecular excitation of the chemical bonds of the gas. The amount of light absorption is proportional to the concentration of the chemical gas in the plumes. The wavelength of the light used for absorption will be selective toward a specific gas, and by changing the wavelength one or more other chemical gases can be detected. Other types of transducers can be used to convert the detection of the analyte to other types of measureable outputs such as physiochemical signals, piezoelectric signals, electrochemical signals, and the like.

In a known chemi-sensor configuration, the recognition element can be a semiconductor film material such as a tin oxide or other highly reactive chemical films that can interact with gas molecules and decompose them. The phrase "target analyte" and variations thereof will be used herein to refer to an ion, a target molecule, or any other chemical substance.

At decision block 206, an inquiry is made as to whether the readings or output data from the first gas sensor exceeds a predetermined threshold. The output data from the first gas sensor represents the gas concentration currently being sensed by the first gas sensor. If the answer to the inquiry at decision block 206 is no, the methodology 200 returns to block 204 to continue monitoring readings from the first gas sensor. If the answer to the inquiry at decision block 206 is yes, the methodology 200 proceeds to block 208 to store various sensor readings in a synchronized manner.

When the plume characterization system 120 (shown in FIG. 1) is implemented in an environment in which the wind turbulence 160 is present, the wind turbulence 160 will dynamically vary the direction of the gas plume 150 in space and time. More specifically, when the wind turbulence 160 is present, the wind turbulence will direct the gas plumes 150 to move along various paths, in various directions, and at various speeds. Accordingly, for a give gas sensor (e.g., the first gas sensor) in a sensor network, the intensity of the gas concentration data output from the first gas sensor will vary in proportion to how much of gas plumes 150 the wind turbulence 160 is currently carrying to the first gas sensor to generate a gas detection. When the output of the first gas sensor spikes, it can be assumed that the wind turbulence 160 is currently blowing some portion of the gas plumes 150 directly into contact with the first gas sensor. In some embodiments of the invention, the processor 140 will initiate or trigger the capture and storage (e.g., block 208) of the first gas sensor output whenever the processor 140 detects that the first gas sensor output exceeds a predetermined threshold. In some embodiments of the invention, the outputs from the first gas sensor are continuously stored, and the processor 140 will initiate a labeling of the captured and stored first gas sensor output whenever the processor 140 detects that the captured and stored first gas sensor output exceeds a predetermined threshold. It is assumed that whenever the concentration measured at a gas sensor spikes above the predetermined level, the air-flow is impacting the plume to hit that sensor.

In some embodiments of the invention, the above-described storage and/or labeling of the first sensor output, which occurs when the first gas sensor output exceeds the predetermined threshold, is facilitated by providing a mechanism that controls the orientation of the first gas sensor in relation to the direction of the wind turbulence 160 that is currently interacting with the first gas sensor. For example, the first gas sensor can be coupled to an orientation device that dynamically reacts to the direction of the wind turbulence 160 in order to adjust the location of the first gas sensor to place the gas sensor in the path of the wind turbulence 160. In some embodiments of the invention, the orientation device can dynamically adjust the location of the first gas sensor such that the first gas sensor's recognition element is facing the direction of the wind turbulence 160.

Without the orientation device described herein, the first gas sensor has to wait until the wind turbulence 160 hits the first gas sensor (and more specifically, hits the first gas sensor's recognition element, which has a delay associated with it called sensor response time) at an appropriate angle while the wind turbulence 160 is carrying enough of the gas plumes 150 to generate a first gas sensor output that is sufficient to exceed the predetermined threshold. If the sensor response time is high (e.g., exceeding a few seconds), recording the wind direction when the sensor response time is maximum may not provide a sufficiently accurate representation of the condition when the plume was carried to the sensor. In some instances, the wind turbulence 160 can carry enough of the gas plumes 150 to the first gas sensor such that a strong first gas sensor output can be generated, but the first gas sensor is pointing in a direction such that the wind turbulence 160 does not contact (or makes insufficient or less than optimal contact with) the recognition element of the first gas sensor. Accordingly, the efficiency and accuracy of the methodology 200 and the plume characterization system 200 are improved by utilizing the orientation mechanism to dynamically adjust the location of the first gas sensor to place the gas sensor in the path of the wind turbulence 160. The efficiency and accuracy of the methodology 200 and the plume characterization system 200 are improved even further by utilizing the orientation mechanism to dynamically adjust the location of the first gas sensor's recognition element such that it substantially faces the direction from which the plume carrying wind turbulence is blowing. In embodiments of the invention, the recognition element is substantially facing the direction from which a wind current is blowing when the wind current strikes the recognition element within an angle that ranges between about +45° and about −45° with respect to a vertical axis that is perpendicular to the face of the recognition element.

Based at least in part on the result of the inquiry in decision block 206 being yes, the methodology 200 moves to block 208 where the processor 140 stores (and/or labels) in a relational database 400 (shown in FIG. 4) the location of the first gas sensor in space; the reading from the first gas sensor that is greater than a predetermined threshold; a synchronized reading from a first wind direction sensor; an optional synchronized reading from a first wind speed sensor; an optional synchronized reading/determination of changes in the wind direction and/or the wind speed; and an optional synchronized first time stamp. In the methodology 200, readings from the first gas sensor in decision block 206 trigger the capture and storage of other readings as described in block 208. In some embodiments of the invention, other sensors/mechanisms (e.g., the orientation control, wind direction, and wind speed sensing system 124 shown in FIG. 1), can be used to trigger the capture and storage of other readings as described in block 208.

The capture and storage of readings taken at block 208 can be synchronized in a variety of ways, including, for example, the location of one sensor relative to another, and the timing of the storage and capture of one reading in relation to the timing of the storage and capture of another reading. For example, the first gas sensor is positionally or spatially synchronized with the first wind direction sensor and the first wind speed sensor by positioning the first wind direction sensor and the first wind speed sensor in relation to the first gas sensor in a manner that ensures that any wind turbulence 160 that carries at least some of the gas plumes 150 to the first gas sensor also impacts and/or interacts with the first wind direction sensor and the first wind speed sensor. In the embodiments of the invention wherein the first gas sensor is movable by an orientation device/mechanism, the positional synchronization of the first gas sensor in relation to the first wind direction sensor and the first wind speed sensor is configured to maintain the positional synchronization when the orientation device/mechanism moves the first gas sensor to align it to substantially face the direction from which the wind turbulence 160 is blowing.

In some embodiments of the invention, the first gas sensor can be positionally or spatially synchronized with the first wind direction sensor and the first wind speed sensor by providing a guide element (e.g., a tube) that carries or guides to the first wind direction sensor and the first wind speed sensor the wind turbulence 160 that carried the gas plumes 150 to the first gas sensor. In some embodiments of the invention, the first gas sensor can be positionally or spatially synchronized with the first wind direction sensor and/or the first wind speed sensor by co-locating in substantially the same plane the sensing surfaces of the first gas sensor, the first wind direction sensor, and/or the first wind speed sensor. The substantially co-planar sensing surfaces are sufficiently small and positioned sufficiently close (e.g., immediately adjacent) to one another that the wind turbulence 160 that carried the gas plumes 150 to the sensing surface of the first gas sensor co-located also impacts the sensing surfaces of the first wind direction sensor and the first wind speed sensor at approximately the same time in approximately the same plane.

Figure 3:
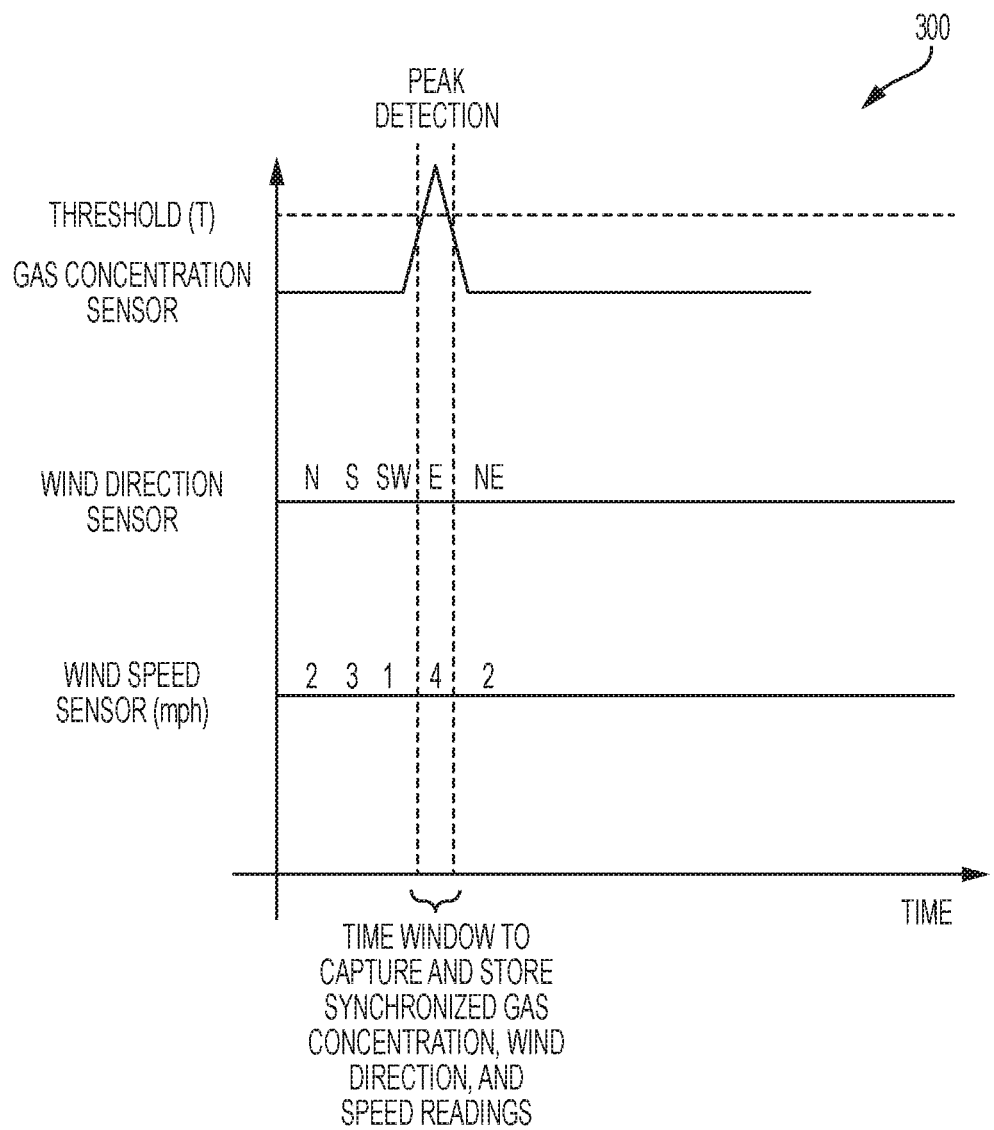
FIG. 3 depicts a timing diagram illustrating aspects of a synchronized sensing methodology according to embodiments of the invention.

In some embodiments of the invention, the first gas sensor can be temporally synchronized with the first wind direction sensor and the first wind speed sensor by capturing and storing time stamp data that corresponds to the time at which the sensor readings described in block 208 are captured and stored. An example is illustrated by the timing diagram 300 shown in FIG. 3, which depicts a window of time to capture and store synchronized gas concentration, wind direction, and wind speed readings/determinations. As shown, the synchronization and capture window is defined by the time during which the first gas sensor reading exceeds the predetermined threshold (T). The time stamp data can include individual time stamp data for each sensor reading or a single time stamp that is logically associated in the relational database 400 (shown in FIG. 4) with the related sensor readings described in block 208. In some embodiments of the invention, the first gas sensor can be positionally or spatially synchronized with the first wind direction sensor and the first wind speed sensor by co-locating in substantially the same plane the sensing surfaces of the first gas sensor, the first wind direction sensor, and/or the first wind speed sensor.

In some embodiments of the invention, the first gas sensor can be logically synchronized with the first wind direction sensor and/or the first wind speed sensor by mapping the logical relationships between the data stored in the relational database 400 (shown in FIG. 4) at block 208 of the methodology 200. For example, through the functionality of the relational database 400, a map is generated that logically maps the location of the first gas sensor in space, the reading from the first gas sensor that is greater than the predetermined threshold, the synchronized reading from the first wind direction sensor, the optional synchronized reading from the first wind speed sensor, and the optional synchronized first time stamp. For example, when the processor 140 needs to access all of the data associated with a reading taken at 9:15 a.m. from the first gas sensor, the processor 140 can access the first gas sensor reading entry in the logical database 400 bearing a 9:15 a.m. timestamp, and use the map to access all of the data that has been logically associated therewith.

The various sensors used to implement the orientation control, wind direction sensing, and wind speed sensing system 124 (shown in FIG. 1), as well as the sensors used in block 208 of the methodology 200, can be implemented in a variety of forms. For example, because the first gas sensor is movable, a dynamic position sensor (e.g., a global positioning system (GPS)) can be used to dynamically track the location of the first gas sensor. The wind orientation device/mechanism and the first wind direction sensor are both used in embodiments of the invention to detect wind direction. The wind orientation device detects wind direction in order to dynamically position the first gas sensor. The first wind direction sensor detects wind direction of the actual wind turbulence 160 that carries the gas plumes 150 to the first gas sensor. Either of the wind orientation device or the first wind direction sensor can be implemented in a variety of ways. For example, they can be an electronic wind direction sensor (e.g., sold under the trade name Firefly™), an electronic compass, a wind vane, a windsock, a configuration of magnets and hall sensors communicatively coupled to a wind vane pivot, an optical encoder communicatively coupled to a wind vane pivot, a pressure sensitive piezoelectric polyvinylidene fluoride (PVDF) material communicatively coupled to a wind vane pivot, and the like. Both the windsock and the wind vane work by moving to minimize air resistance. The direction in which a wind vane is pointed by prevailing winds indicates the direction from which the wind is blowing. The larger opening of a windsock faces the direction that the wind is blowing from, and its tail, with the smaller opening, points in the same direction as the wind is blowing. The first wind speed sensor can be implemented in a variety of ways, including, for example, a pitot tube communicatively coupled to a pressure transducer, an anemometer, and the like.

Blocks 212, 214, 216 execute in the same manner as described above in connection with blocks 204, 206, 208 except the operations in block 212, 214, 216 are implemented using a second gas sensor, a second wind direction sensor, a second wind speed sensor, and a second set of time stamp data. The data that has been captured and stored at blocks 208, 216 are now available to be accessed by the processing algorithms identified at block 210. In block 210, the processor 140 accesses the readings/determinations captured and stored at blocks 208, 216 and implements a process to estimate a location of a leak at the gas source 110 (shown in FIG. 1) that is the source of the gas plumes 150 (shown in FIG. 1).

A wide variety of processing/analysis algorithms can be used to implement block 210. In some embodiments of the invention, the methodology 200 implements block 210 by using algorithms that includes among their operations using the reading at block 206, the location of the first gas sensor at the time of the first gas sensor reading, and the direction of the wind turbulence 160 that carried the gas plume 150 to the first gas sensor at the time of the first gas sensor reading to identify a first line identifying a portion of the path along which the turbulence 160 and the plume 150 has traveled. The methodology 200 further implements block 210 by using algorithms that includes among their operations using the reading at block 214, the location of the second gas sensor at the time of the second gas sensor reading, and the direction of the wind turbulence 160 that carried the gas plume 150 to the second gas sensor at the time of the second gas sensor reading to identify a second line identifying a portion of the path along which the turbulence 160 and the plume 150 has traveled. The methodology 200 applies the operations at blocks 206, 208, 212, 214 to additional sensors to develop additional lines, and the intersections of the various lines are plotted as part of the algorithm processing that is used to estimate the location of the gas leak.

In embodiments of the invention, the plume characterization system 120 (shown in FIG. 1) can implement methodology 200 in a manner that implements a predictive synchronization between different sensors. For example, one set of sensors can detect concentration, wind direction and wind speed in one locations at a moment of time. Based at least in part on wind direction change, the system 120 can, based at least in part on detected concentration, wind direction and wind speed, pass the detection function to another set of sensors in the sensor network that the system 120 has predicted will be in the path of the new wind direction. In embodiments of the invention, the data acquisition functions can be shut down on the original set of sensors, and a new data acquisition can be triggered at the set of sensors that the system 120 has predicted will be in the path of the new wind direction. In embodiments of the invention, the predictive functionality can be implemented by providing the processor system 140 (shown in FIG. 1) with machine learning functionality, which can include machine learning algorithms, training data, actual training data measured by the sensor sets, predictive engines, and the like, configured to learn from training data and actual data to predict the next sensor set that will be in the path of wind turbulence 160 that is carrying the plume 150. In embodiments of the invention, the system 120 (e.g., the processor system 140) is configured to be aware of the location of the sensor sets in the sensor network, along with the relative orientations of the sensor sets across an area while timing of each sensor set is being predictively synchronized.

In embodiments of the invention, the plume characterization system 120 can implement methodology 200 such that the data acquisition frequency is triggered by the rate of change in chemical plume concentration and/or the wind direction change. For example, if the chemical plume concentration is increasing, the data acquisition rate is increasing. Similarly, if the chemical plume concentration is decreasing, the data acquisition frequency will decrease. With an integrated and synchronized sensing (e.g., system 130 shown in FIG. 1) in accordance with embodiments of the invention, both the plume concentration and the direction of the wind that carries the plum concentration can be captured with one system.

Accordingly, the efficiency and accuracy of the methodology 200 at block 210 can be improved by utilizing the structures and method of the present invention to synchronize sensing operations such that the gas sensor is aligned with the direction of the wind that is carrying a plume to the gas sensor; the capture and storage of gas sensor readings are synchronized to occur when the gas sensor is aligned with the direction of the actual wind current that carries the plume; and the direction of the actual wind current that is carrying the plume to the gas sensor is captured. The efficiency and accuracy of the methodology 200 can be improved even further by incorporating wind speed into the processing performed at block 210.

Figure 5:
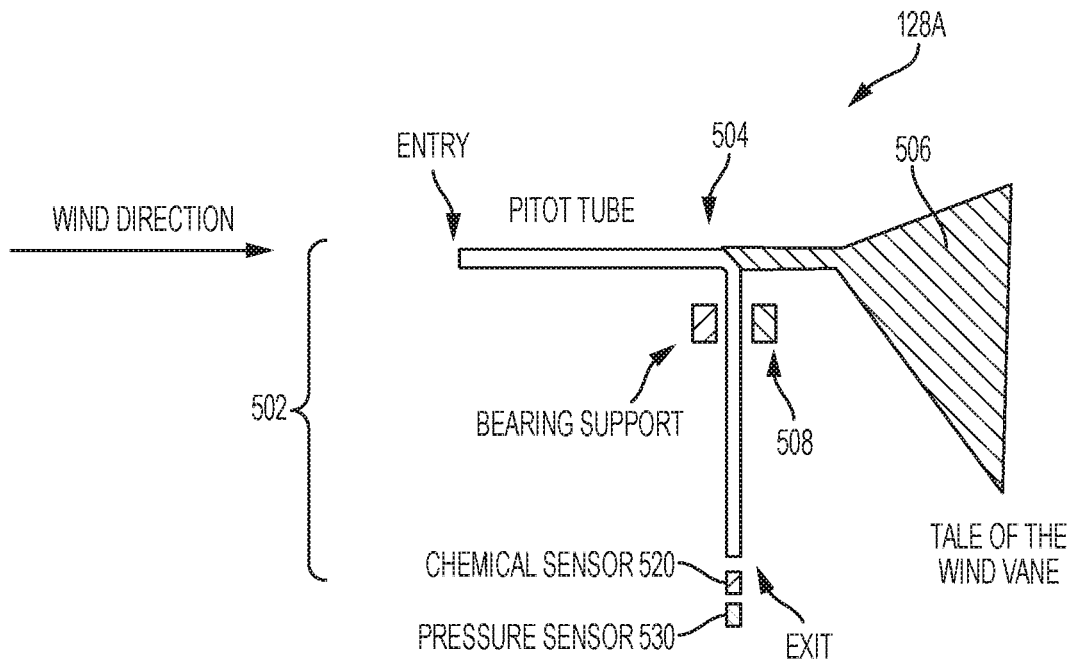
FIG. 5 depicts a schematic diagram of a portion of a plume characterization system according to embodiments of the invention.

FIG. 5-10 depict non-limiting examples of components that can be used to implement portions of the plume characterization system 120 shown in FIG. 1. More specifically, FIG. 5 depicts an example in which the integrated & synchronized wind/gas sensing system 128 is implemented as an integrated & synchronized wind/gas sensing system 128A having a wind vane 502, a chemical sensor 520, and a pressure sensor 530, configured and arranged as shown. The wind vane 502 is formed from a pitot tube 504, a tail component 506, and a bearing support 508, configured and arranged as shown. The pitot tube 502 can freely rotate on the bearing support 508 as the wind striking the wind vane 502 changes its orientation. A gas entry end of the pitot tube 504 functions as the head of the wind vane 502, and the chemical/pressure sensors 520, 530 are positioned at the gas exit end of the pitot tube 504. Accordingly, the wind vane 128A continuously and dynamically repositions the pitot tube 504 such that the gas entry end of the pitot tube 504 is always facing the direction from which the wind that impacts the wind vane 502 is blowing.

The sensors 520, 530 are mounted on the wind vane 502, which is configured to align with the direction from which the wind (e.g., wind turbulence 160 (shown in FIG. 1)) that impacts the wind vane 502 is blowing. The sensors 520, 530 are positioned on the wind vane 502 such that the wind vane 502 will dynamically position the sensors 520, 530 to face the direction from which the wind is blowing. The chemical sensor 520 can be implemented as a so-called "chemi-sensor" in which a semiconductor transistor acts as a transducer separated by an insulator layer (e.g. $SiO_2$) from a chemical recognition element that is selective to the target molecule (i.e., the analyte). Other types of transducers can be used to convert the detection of the analyte to other types of measureable outputs such as optical signals, physio-chemical signals, piezoelectric signals, electrochemical signals, and the like.

In embodiments of the invention, the pitot tube 504 can be implemented as a hollow tube. A benefit of using the pitot tube 504 is that the pitot tube 504 and the pressure sensor 530 can be used as a wind speed sensor that measures the speed of the wind (e.g., wind turbulence 160 (shown in FIG. 1)) that is currently impacting and setting the position of the wind vane 502. The pressure sensor 530 can be configured to translate pressure into an electrical signal that corresponds to the wind speed. Another benefit of using the pitot tube 504 is that it can measure the wind speed while the wind vane 502 orient the gas entry end of the pitot tube 504 against the wind direction. Yet another benefit of the pitot tube 504 is to make sure that the chemical gas that reaches the chemi-sensor 520 is carried by the wind and is not back-propagating from a source and being diffused toward the sensor. Because the orientation of the pitot tube 504 is toward the wind, it will always sample the atmosphere that is moved by the wind, thereby improving the source localization analytics (e.g., block 210 shown in FIG. 2).

Figure 6:
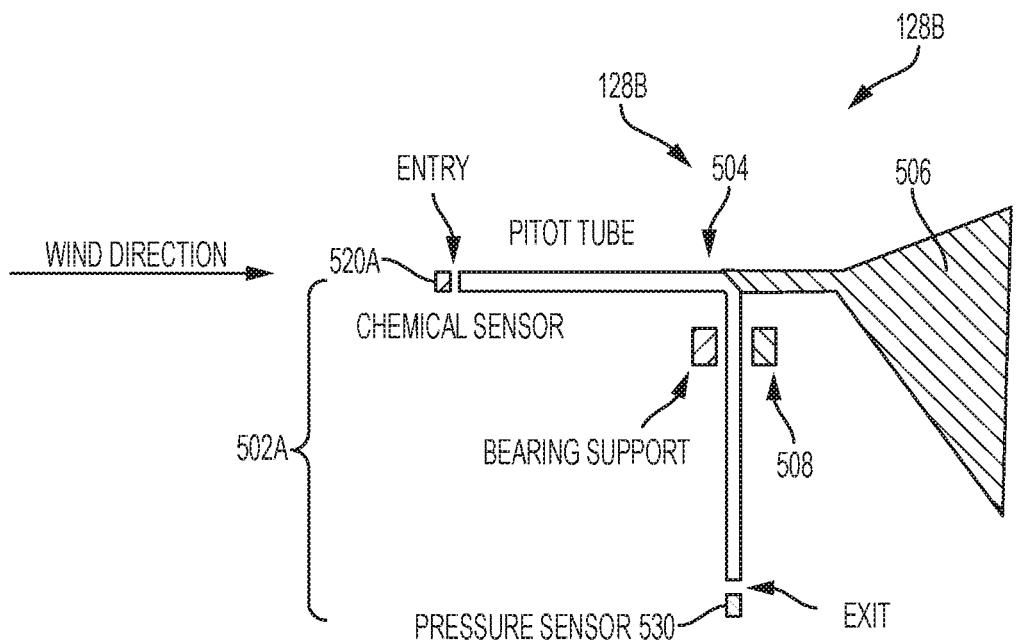
FIG. 6 depicts a schematic diagram of a portion of a plume characterization system according to embodiments of the invention.

FIG. 6 depicts an integrated & synchronized wind/gas sensing system 128B that is identical to the integrated & synchronized wind/gas sensing system 128A except that the wind vane 502A provides a chemical sensor 520A positioned at the gas entry end of the pitot tube 504. A benefit of positioning the chemical sensor 520A at the gas entry end of the pitot tube 504 is that the chemical sensor 520A at the gas entry end of the pitot tube 504 will sample the concentration of analytes in the unimpeded air-flow. When the chemical sensor 520 (shown in FIG. 5) is at the exit end of the pitot tube 504, the air-flow that carries the gas plumes 150 (shown in FIG. 1) can experience some gas concentration dilution as the air-flow and gas plumes 150 move through the pitot tube 504 toward the exit end and the chemical sensor 520.

The pressure sensor 530 can be positioned at the gas entry end or the gas exit end of the pitot tube 504. In the examples illustrated in FIGS. 5 and 6, the pressure sensor 530 can be calibrated to compensate for any pressure dilution that occurs as air-flow travels from the gas entry end to the gas exit end of the pitot tube 504. If the pressure sensor 530 is positioned at the gas entry end of the pitot tube 504, it may or may not be necessary to pass the wires that power the pressure sensor 530 through the pitot tube 504. Because the pitot tube 504 and the wires will rotate along with the vane tail 506, this rotation can cause the wires to become damaged over time. Mounting the present sensor 530 at the exit end of the pitot tube 504 has the benefit of eliminating the need to run wiring through the wind vane 502. The pressure sensor 530 at the exit end of the pitot tube 504 will still measure the gas plumes 150 that are blown to and captured by the pitot tube 504, but wind travel through the pitot tube 504 needs to be compensated such that all measurement are synchronized (by time, position, etc.).

Figure 7A:
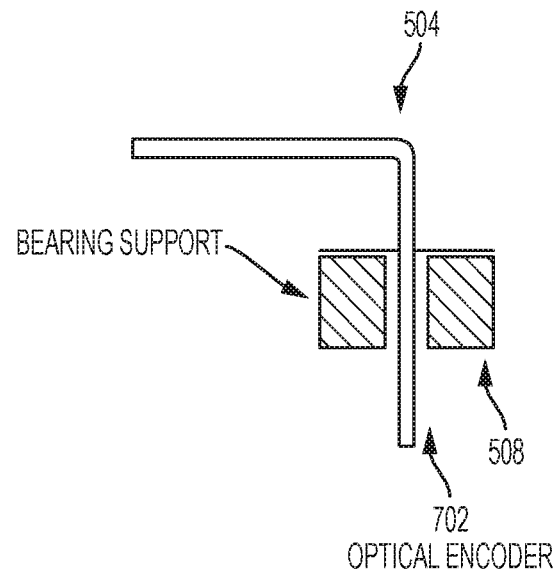
FIG. 7A depicts a schematic diagram of a portion of a plume characterization system according to embodiments of the invention.

FIG. 7A depicts an isolated view of the bearing support 508 and the pitot tube 504 having an optical encoder 702 communicatively coupled at the bearing support 508, wherein the optical encoder 702 is configured to capture wind direction measurements by tracking rotation of the pitot tube 504 in relation to the bearing support 508. The optical encoder 702 can be configured to measure angles from 0° to 360° with accuracy down to 0.1°.

Figure 7B:
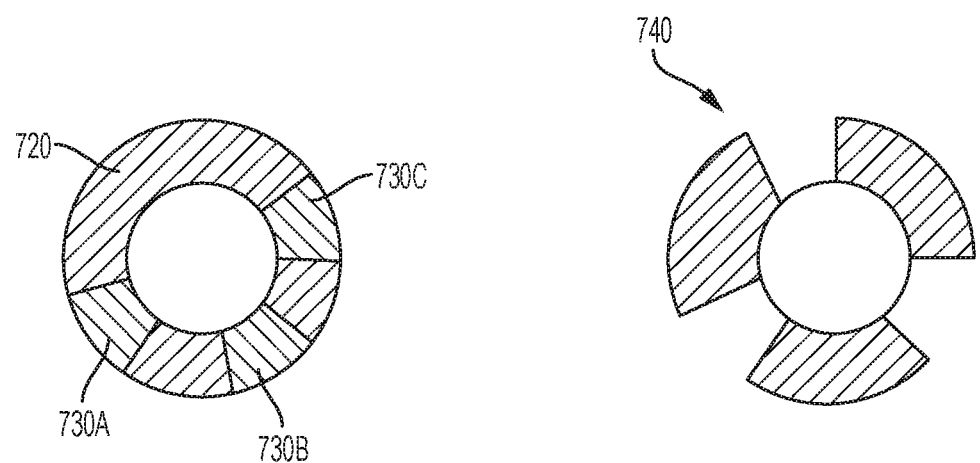
FIG. 7B depicts a schematic diagram of a portion of a plume characterization system according to embodiments of the invention.

FIG. 7B depicts a magnetic encoder (720, 730A, 730B, 730C, 740) that can be used to track rotation of the pitot tube 504 (shown in FIG. 7A) in relation to the bearing support 508 (shown in FIG. 7A) to provide wind direction measurements. The magnetic encoder includes a three piece magnetic block 740 on the top. The top part 740 is connected rigidly to the wind vane 502 (shown in FIGS. 5 and 6). As the top part 740 is rotated by the wind torque, the position of the magnet 720 at the bottom of the bearing 508 induces an increased signal in the Hall-based sensors 730A, 730B, 730C that are integrated into the bearing 508. The signal generated by the Hall-based sensor 730A, 730B, 730C are proportional with the area of its top surface covered by the magnet. When the top surface 740 is rotating, the signal generated by the Hall-based sensors 730A, 730B, 730C will increase/decrease in proportion to the position of the wind vane 502 (and hence the direction of the wind).

The multiple Hall-based sensors 730A, 730B, 730C are mounted along the magnets 720 in the bottom of the bearing 508 while the top part 720 of the bearing 508 is just a patterned doughnut-shaped magnet. The Hall-based sensors 730A, 730B, 730C are mounted in a non-regular pattern such the magnetic signal can be detected when the top magnet 740 is positioned above one of the Hall-based sensors 730A, 730B, 730C, or provide no signal if the magnet 740 is not positioned above one of the Hall-based sensors 730A, 730B, 730C. In embodiments of the invention, the top and bottom magnets 740, 720 can be configured to have opposite magnetic poles. In embodiments of the invention, the top and bottom magnets 740, 720 can be mounted around a rigid shaft that passes through the middle of the rings formed by the top and bottom magnets 740, 720 so that the top and bottom magnets 740, 720 repeal each other they are floating on the top of each other. The voltage on the Hall-based sensors 730A, 730B, 730C is increased when one magnet is above one of the Hall-based sensors 730A, 730B, 730C, or the voltage on the Hall-based sensors 730A, 730B, 730C will generate "no signal" if a magnet is not above one of the Hall-based sensors 730A, 730B, 730C. Increasing the number of integrated Hall-based sensors can improve the accuracy of the ultimate wind direction detection/determination.

Figure 8A:
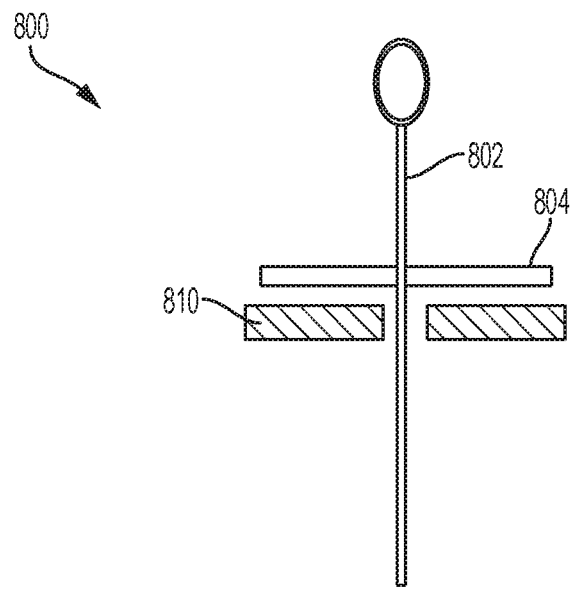
FIG. 8A depicts a schematic diagram of a portion of a plume characterization system according to embodiments of the invention.
Figure 8B:
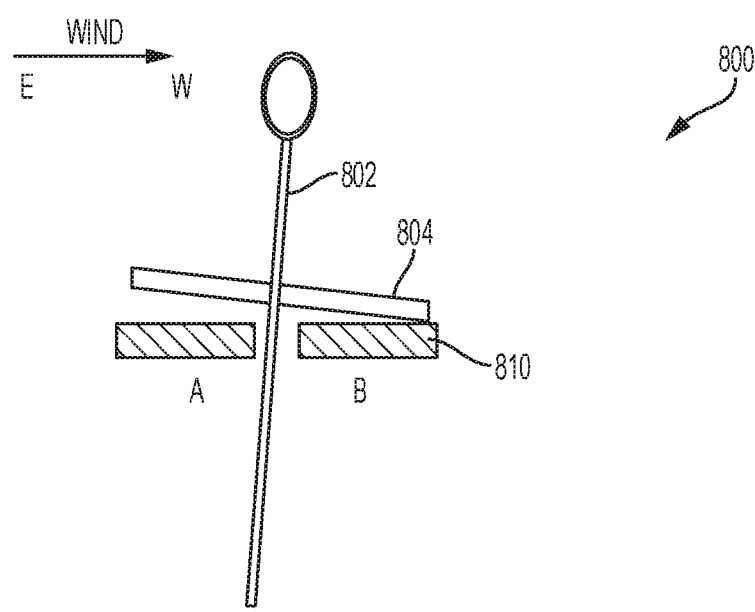
FIG. 8B depicts a schematic diagram of a portion of a plume characterization system according to embodiments of the invention.

FIGS. 8A and 8B depict another example of a wind direction sensor 800 capable of being implemented in connection with the integrated wind/gas sensing system 128 (shown in FIG. 1). The wind direction sensor 800 includes a rigid shaft 802, a plate 804, and a pressure sensitive PVDF film 810, configured and arranged as shown. The shaft 802 is rigidly secured to the plate 804. However, the shaft 802 and the plate 804 are configured to be movable in relation to the PVDF film 810. The wind direction sensor 800 is shown in FIG. 8A in its steady state. The wind direction sensor 800 is shown in FIG. 8B under the influence of a wind current blowing from east (E) to west (W). In the steady state shown in FIG. 8A, the plate 804 stays parallel to the PVDF film 810. When wind is blowing (e.g., from east to west as shown in FIG. 8B), the wind tilts the shaft 802, which pushes the plate 804 against a particular region (or a particular set of elements) of the pressure sensitive PVDF film 810. The location and orientation of the contacted regions/elements of the pressure sensitive PVDF film 810 correspond to the direction of the wind current that moved the shaft 802. In response to pressure applied thereto caused by the E-W wind currents, the PVDF film 810 generates a voltage from the elements of the PVDF film 810 that contact the plate 804. During the E-W wind current, the elements of the PVDF film 810 that are not contacting the plate 804 do not generate a voltage. In embodiments of the invention, the parallel steady state of the plate 804 can be maintained by a magnetic bearing (e.g., as shown in FIGS. 7A and 7B) or by a gimbal.

FIG. 9 depicts a circuit 900, which can be coupled to the PVDF film 810 (shown in FIG. 8B) to generate a $V_{OUT}$. The circuit 900 is comparator circuit that uses an operational amplifier 902 to compare one analog voltage level ($V_A$) with another analog voltage level ($V_B$) and produce an output signal ($V_{OUT}$) based on this voltage comparison. In other words, the operational amplifier/voltage comparator circuit 900 compares the magnitudes of two voltage inputs and determines which is the larger of the two. In the example shown in FIGS. 8B and 9, $V_B$ (which results from applied pressure) is greater than $V_A$ (which results from no applied pressure) so $V_{OUT}$ is substantially equal to $V_A$ (which represents the E-W direction of the wind).

FIG. 10 depicts another example of a wind direction sensor 1000 capable of being implemented in connection with the integrated wind/gas sensing system 128 (shown in FIG. 1). The wind direction sensor 1000 includes a rigid shaft 1002, a disk/plate 1004, and a pressure sensitive PVDF film 1010, configured and arranged as shown. The pressure sensitive PVDF film 1010 is arranged in quadrants (A, B, C, D) for better measurement granularity. The shaft 1002 is rigidly secured to the disk 1004. However, the shaft 1002 and the disk 1004 are configured to be movable in relation to the PVDF film 1010. The wind direction sensor 1000 operates in substantially the same way as the wind direction sensor 800 shown in FIGS. 8A and 8B. In some situations, the disk 1004 can press more than one of the PVDF quadrants (A, B, C, D) at the same time, which would result in a medium wind direction (e.g., an east/west wind direction).

FIG. 11 depicts another example of a wind direction sensor 1100 capable of being implemented in connection with the integrated wind/gas sensing system 128 (shown in FIG. 1). The wind direction sensor 1100 includes a rigid shaft 1102, a disk/plate 1104, and a pressure sensitive PVDF film 1110, configured and arranged as shown. The pressure sensitive PVDF film 1110 is arranged in a pattern of semi-circle segments for better measurement granularity. The granularity of the direction measurements can be increased by increasing the number of semicircle segments. The shaft 1102 is rigidly secured to the disk 1104. However, the shaft 1102 and the disk 1104 are configured to be movable in relation to the PVDF film 1110. The wind direction sensor 1100 operates in substantially the same way as the wind direction sensor 800 shown in FIGS. 8A and 8B. In some situations, the disk 1104 can press more than one of the PVDF semicircular segments at the same time, which would result in a medium wind direction (e.g., a wind direction between 270° and 360°). The semicircular segments 1110 of the sensor 1100 can detect wind direction within a sensitivity of 90°. In embodiments of the invention, the size and proximity of the semicircular segments 1110 will determine the resolution of the ultimate detection (i.e., the smallest detectable angle).

Thus, it can be seen from the foregoing detailed description that embodiments of the invention provide technical effects and benefits. For example, the chemical detection system described herein can be used to take substantially simultaneous measurement of the wind direction and a chemical reading from point sensors. The point sensors can be part of a wireless sensor network that collects data from all sensing points and sends the data to a cloud computing system. Alternatively, the signal can be processed at the point of acquisitions and just the integrated values are sent to the cloud in order to not overwhelm the available communications bandwidth. The measurements can be aggregated over a period of time to extract mean wind direction for each chemical detection event. The measurement of chemical detection events can be used to quantify the leak rate and potential location of the leak based at least in part on data aggregation from multiple sensors. Signals from the sensor can warn an operator about malfunctioning equipment on the well pad that has a leak. The signal can also be used as a warning that is sent to people carrying out maintenance work on the well pad to avoid areas that may or may not have chemical concentrations above predetermined limits. The signal from the sensor can automatically trigger a work order to initiate repair work. Based on the detected size of the leak, the signal can dispatch a crew immediately if it is determined that the leak is large and potentially more dangerous than a smaller leak.

The following definitions and abbreviations are to be used for the interpretation of the claims and the specification. As used herein, the terms "comprises," "comprising," "includes," "including," "has," "having," "contains" or "containing," or any other variation thereof, are intended to cover a non-exclusive inclusion. For example, a composition, a mixture, process, method, article, or apparatus that comprises a list of elements is not necessarily limited to only those elements but can include other elements not expressly listed or inherent to such composition, mixture, process, method, article, or apparatus.

Additionally, the term "exemplary" is used herein to mean "serving as an example, instance or illustration." Any embodiment or design described herein as "exemplary" is not necessarily to be construed as preferred or advantageous over other embodiments or designs. The terms "at least one" and "one or more" are understood to include any integer number greater than or equal to one, i.e. one, two, three, four, etc. The terms "a plurality" are understood to include any integer number greater than or equal to two, i.e. two, three, four, five, etc. The term "connection" can include an indirect "connection" and a direct "connection."

References in the specification to "one embodiment," "an embodiment," "an example embodiment," etc., indicate that the embodiment described can include a particular feature, structure, or characteristic, but every embodiment may or may not include the particular feature, structure, or characteristic. Moreover, such phrases are not necessarily referring to the same embodiment. Further, when a particular feature, structure, or characteristic is described in connection with an embodiment, it is submitted that it is within the knowledge of one skilled in the art to affect such feature, structure, or characteristic in connection with other embodiments whether or not explicitly described.

The terms "about," "substantially," "approximately," and variations thereof, are intended to include the degree of error associated with measurement of the particular quantity based upon the equipment available at the time of filing the application. For example, "about" can include a range of ±8% or 5%, or 2% of a given value.

It is understood in advance that although a detailed description on cloud computing is provided, implementation of the teachings recited herein are not limited to a cloud computing environment. Rather, embodiments of the present invention are capable of being implemented in conjunction with any other type of computing environment now known or later developed.

Cloud computing is a model of service delivery for enabling convenient, on-demand network access to a shared pool of configurable computing resources (e.g. networks, network bandwidth, servers, processing, memory, storage, applications, virtual machines, and services) that can be rapidly provisioned and released with minimal management effort or interaction with a provider of the service. This cloud model may include at least five characteristics, at least three service models, and at least four deployment models.

Characteristics are as follows:

On-demand self-service: a cloud consumer can unilaterally provision computing capabilities, such as server time and network storage, as needed automatically without requiring human interaction with the service's provider.

Broad network access: capabilities are available over a network and accessed through standard mechanisms that promote use by heterogeneous thin or thick client platforms (e.g., mobile phones, laptops, and PDAs).

Resource pooling: the provider's computing resources are pooled to serve multiple consumers using a multi-tenant model, with different physical and virtual resources dynamically assigned and reassigned according to demand. There is a sense of location independence in that the consumer generally has no control or knowledge over the exact location of the provided resources but may be able to specify location at a higher level of abstraction (e.g., country, state, or datacenter).

Rapid elasticity: capabilities can be rapidly and elastically provisioned, in some cases automatically, to quickly scale out and rapidly released to quickly scale in. To the consumer, the capabilities available for provisioning often appear to be unlimited and can be purchased in any quantity at any time.

Measured service: cloud systems automatically control and optimize resource use by leveraging a metering capability at some level of abstraction appropriate to the type of service (e.g., storage, processing, bandwidth, and active user accounts). Resource usage can be monitored, controlled, and reported providing transparency for both the provider and consumer of the utilized service.

Service Models are as follows:

Software as a Service (SaaS): the capability provided to the consumer is to use the provider's applications running on a cloud infrastructure. The applications are accessible from various client devices through a thin client interface such as a web browser (e.g., web-based e-mail). The consumer does not manage or control the underlying cloud infrastructure including network, servers, operating systems, storage, or even individual application capabilities, with the possible exception of limited user-specific application configuration settings.

Platform as a Service (PaaS): the capability provided to the consumer is to deploy onto the cloud infrastructure consumer-created or acquired applications created using programming languages and tools supported by the provider. The consumer does not manage or control the underlying cloud infrastructure including networks, servers, operating systems, or storage, but has control over the deployed applications and possibly application hosting environment configurations.

Infrastructure as a Service (IaaS): the capability provided to the consumer is to provision processing, storage, networks, and other fundamental computing resources where the consumer is able to deploy and run arbitrary software, which can include operating systems and applications. The consumer does not manage or control the underlying cloud infrastructure but has control over operating systems, storage, deployed applications, and possibly limited control of select networking components (e.g., host firewalls).

Deployment Models are as follows:

Private cloud: the cloud infrastructure is operated solely for an organization. It may be managed by the organization or a third party and may exist on-premises or off-premises.

Community cloud: the cloud infrastructure is shared by several organizations and supports a specific community that has shared concerns (e.g., mission, security requirements, policy, and compliance considerations). It may be managed by the organizations or a third party and may exist on-premises or off-premises.

Public cloud: the cloud infrastructure is made available to the general public or a large industry group and is owned by an organization selling cloud services.

Hybrid cloud: the cloud infrastructure is a composition of two or more clouds (private, community, or public) that remain unique entities but are bound together by standardized or proprietary technology that enables data and application portability (e.g., cloud bursting for load-balancing between clouds).

A cloud computing environment is service oriented with a focus on statelessness, low coupling, modularity, and semantic interoperability. At the heart of cloud computing is an infrastructure comprising a network of interconnected nodes.

Figure 12:
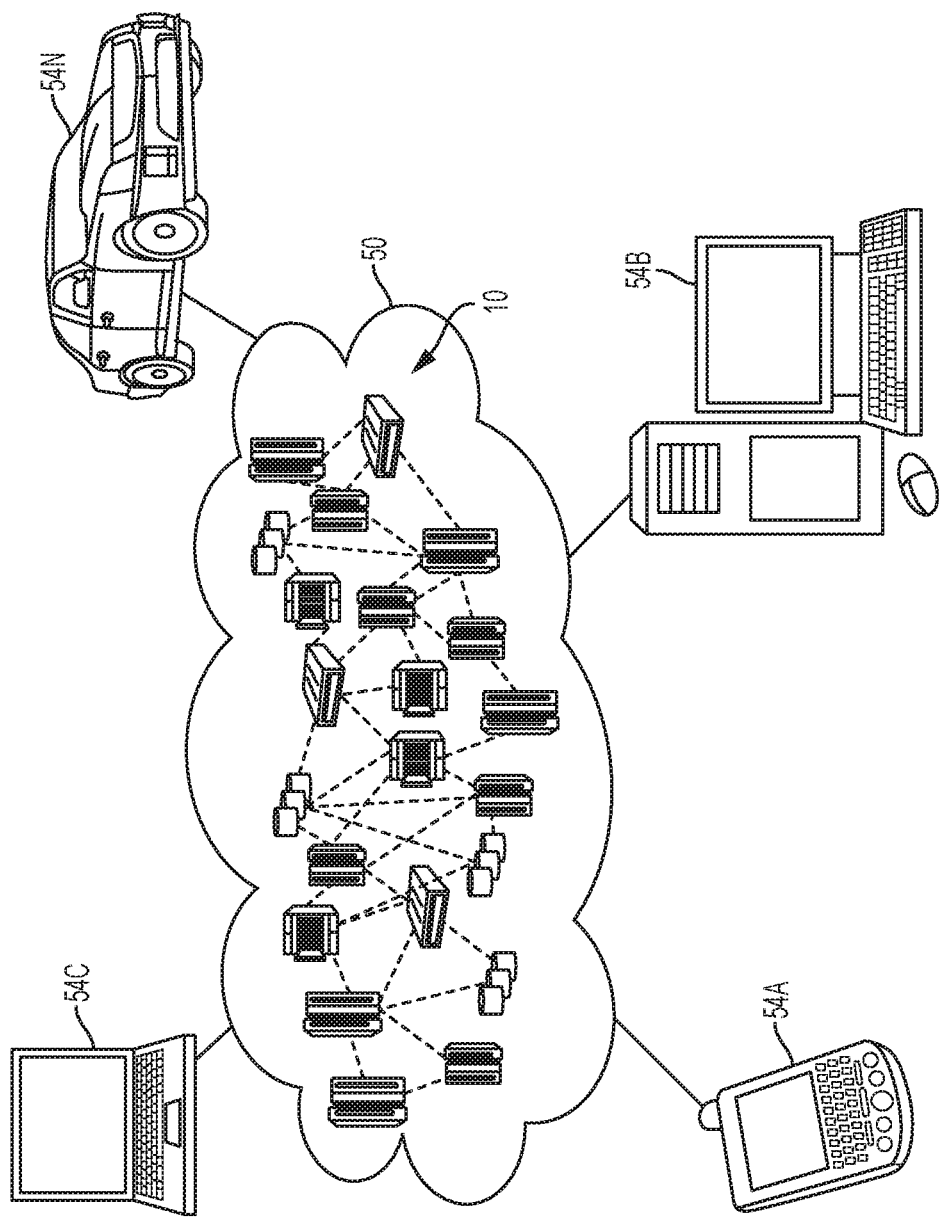
FIG. 12 depicts a cloud computing environment according to embodiments of the invention.

Referring now to FIG. 12, illustrative cloud computing environment 50 is depicted. As shown, cloud computing environment 50 comprises one or more cloud computing nodes 10 with which local computing devices used by cloud consumers, such as, for example, personal digital assistant (PDA) or cellular telephone 54A, desktop computer 54B, laptop computer 54C, and/or automobile computer system 54N may communicate. Nodes 10 may communicate with one another. They may be grouped (not shown) physically or virtually, in one or more networks, such as Private, Community, Public, or Hybrid clouds as described hereinabove, or a combination thereof. This allows cloud computing environment 50 to offer infrastructure, platforms and/or software as services for which a cloud consumer does not need to maintain resources on a local computing device. It is understood that the types of computing devices 54A-N shown in FIG. 12 are intended to be illustrative only and that computing nodes 10 and cloud computing environment 50 can communicate with any type of computerized device over any type of network and/or network addressable connection (e.g., using a web browser).

Figure 13:
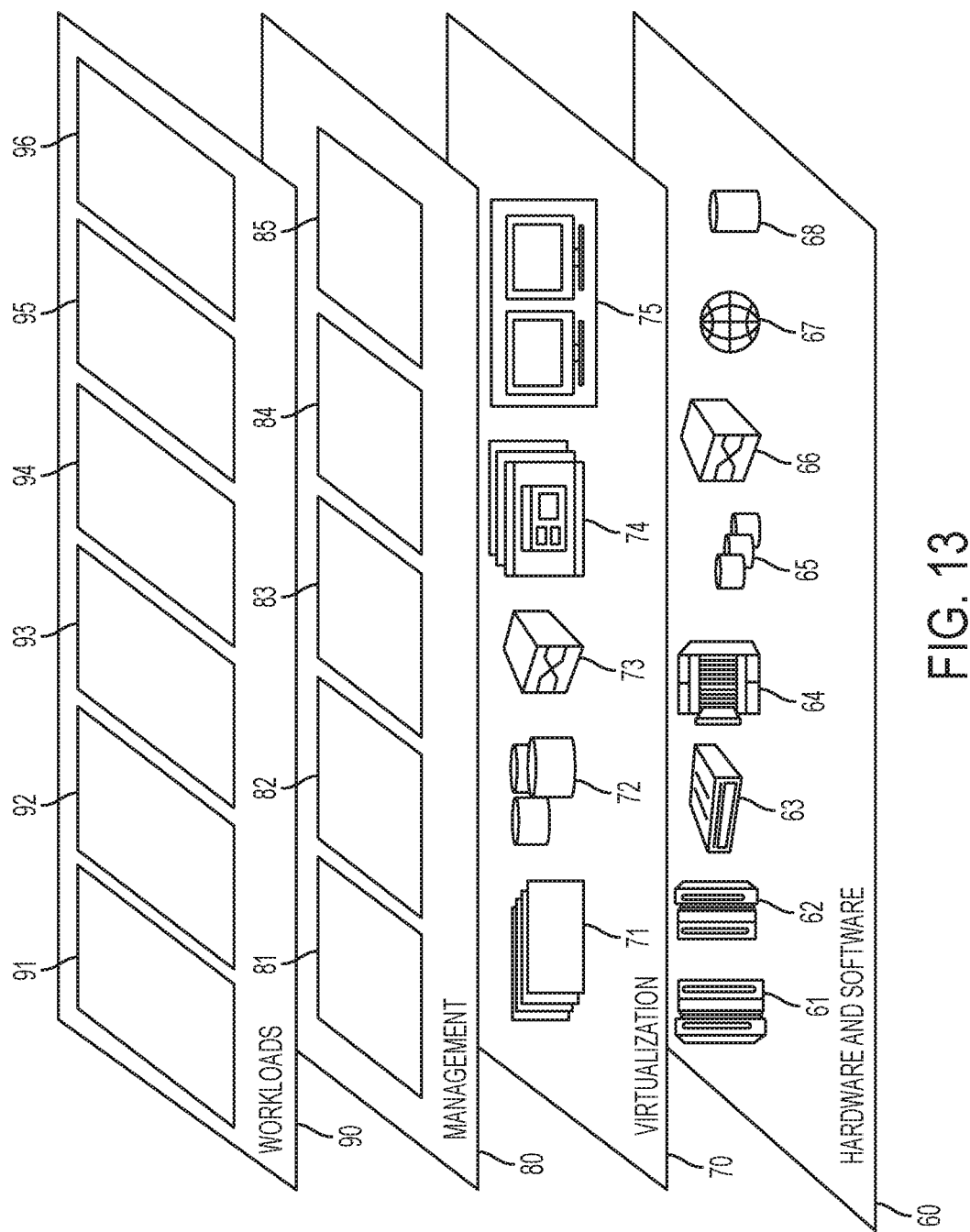
FIG. 13 depicts abstraction model layers according to embodiments of the invention.

Referring now to FIG. 13, a set of functional abstraction layers provided by cloud computing environment 50 (FIG. 12) is shown. It should be understood in advance that the components, layers, and functions shown in FIG. 13 are intended to be illustrative only and embodiments of the invention are not limited thereto. As depicted, the following layers and corresponding functions are provided:

Hardware and software layer 60 includes hardware and software components. Examples of hardware components include: mainframes 61; RISC (Reduced Instruction Set Computer) architecture based servers 62; servers 63; blade servers 64; storage devices 65; and networks and networking components 66. In some embodiments, software components include network application server software 67 and database software 68.

Virtualization layer 70 provides an abstraction layer from which the following examples of virtual entities may be provided: virtual servers 71; virtual storage 72; virtual networks 73, including virtual private networks; virtual applications and operating systems 74; and virtual clients 75.

In one example, management layer 80 may provide the functions described below. Resource provisioning 81 provides dynamic procurement of computing resources and other resources that are utilized to perform tasks within the cloud computing environment. Metering and Pricing 82 provide cost tracking as resources are utilized within the cloud computing environment, and billing or invoicing for consumption of these resources. In one example, these resources may comprise application software licenses. Security provides identity verification for cloud consumers and tasks, as well as protection for data and other resources. User portal 83 provides access to the cloud computing environment for consumers and system administrators. Service level management 84 provides cloud computing resource allocation and management such that required service levels are met. Service Level Agreement (SLA) planning and fulfillment 85 provide pre-arrangement for, and procurement of, cloud computing resources for which a future requirement is anticipated in accordance with an SLA.

Workloads layer 90 provides examples of functionality for which the cloud computing environment may be utilized. Examples of workloads and functions which may be provided from this layer include: mapping and navigation 91; software development and lifecycle management 92; virtual classroom education delivery 93; data analytics processing 94; transaction processing 95; and plume characterization system 96.

Figure 14:
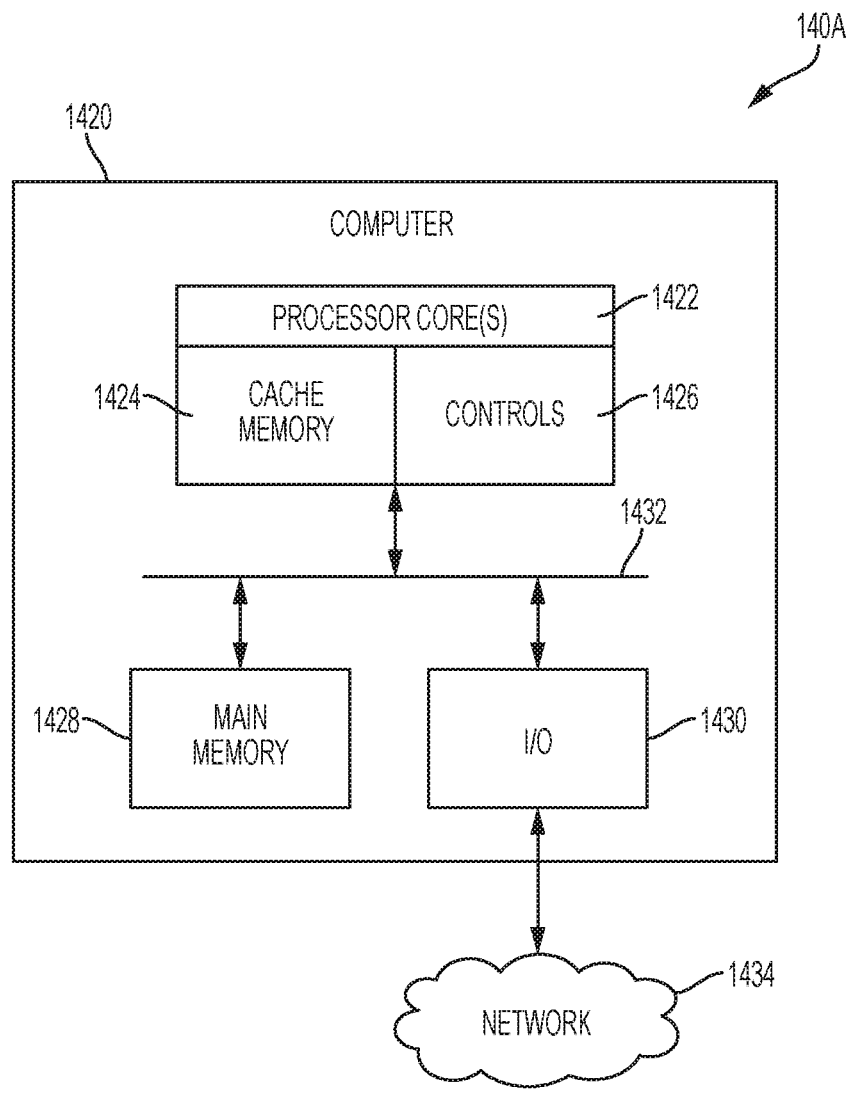
FIG. 14 depicts a computer system for implementing aspects of the invention.

FIG. 14 depicts a more detailed example of how the processor 140 (shown in FIG. 1) can be implemented as a computer system 140A including an exemplary computing device ("computer") 1420 configured to receive outputs from the integrated & sensing wind/gas sensing system 140 (shown in FIG. 1) and process/analyze the same in accordance with aspects of the present invention. In addition to computer 1420, exemplary computer system 140A includes network 1434, which connects computer 1420 to additional systems (not depicted) and can include one or more wide area networks (WANs) and/or local area networks (LANs) such as the Internet, intranet(s), and/or wireless communication network(s). Computer 1420 and additional systems are in communication via network 1434, e.g., to communicate data between them.

Exemplary computer 1420 includes processor cores 1422, main memory ("memory") 1428, and input/output component(s) 1430, which are in communication via bus 1432. Processor cores 1422 includes cache memory ("cache") 1424 and controls 1426. Cache 1424 can include multiple cache levels (not depicted) that are on or off-chip from processor 1422. Memory 1424 can include various data stored therein, e.g., instructions, software, routines, etc., which, e.g., can be transferred to/from cache 1424 by controls 1426 for execution by processor 1422. Input/output component(s) 1430 can include one or more components that facilitate local and/or remote input/output operations to/from computer 1420, such as a display, keyboard, modem, network adapter, etc. (not depicted).

The present invention may be a system, a method, and/or a computer program product. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the present invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

The terminology used herein is for the purpose of describing particular embodiments only and is not intended to be limiting of the present invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, element components, and/or groups thereof.

The corresponding structures, materials, acts, and equivalents of all means or step plus function elements in the claims below are intended to include any structure, material, or act for performing the function in combination with other claimed elements as specifically claimed. The description of the present invention has been presented for purposes of illustration and description, but is not intended to be exhaustive or limited to the invention in the form disclosed. Many modifications and variations will be apparent to those of ordinary skill in the art without departing from the scope and spirit of the invention. The embodiment was chosen and described in order to best explain the principles of the invention and the practical application, and to enable others of ordinary skill in the art to understand the invention for various embodiments with various modifications as are suited to the particular use contemplated.

What is claimed is:

1. An integrated sensing system comprising:
   a movable orientation device configured to dynamically position the movable orientation device based at least in part on receiving turbulent air-flow; and
   a gas sensor coupled to the movable orientation device;
   wherein the gas sensor comprises a recognition element configured to detect a chemical in a plume;
   wherein the movable orientation device is configured to perform a synchronized sensing operation comprising:
      based at least in part on the movable orientation device receiving the turbulent air-flow, moving the movable orientation device to dynamically maintain a predetermined orientation of the movable orientation device relative to a direction of the turbulent air-flow;
      wherein the predetermined orientation comprises positioning the recognition element of the gas sensor in a path of the turbulent air-flow to expose the recognition element to a turbulent-air-flow impacted plume comprising the plume moving in the path under influence of the turbulent air-flow.

2. The system of claim 1, wherein:
   the recognition element comprises a primary sensing surface; and
   the synchronized sensing operation further comprises, based at least in part on detecting the direction of the turbulent air-flow that is influencing the plume to move in the path, positioning the gas sensor relative to the path such that the primary sensing surface substantially faces the direction of the turbulent air-flow.

3. The system of claim 1, wherein:
   the gas sensor is further configured to generate plume composition data based at least in part on the recognition element detecting the chemical in the plume; and
   the system is further configured to:
      detect a change in a chemical composition detected by the gas sensor; and
      trigger a data acquisition rate of other sensors to change as the chemical concentration decreases or increases.

4. The system of claim 3, wherein:
   the system further comprises an air-flow direction sensor coupled to the movable orientation device; and
   the air-flow direction sensor is configured to generate air-flow direction data based at least in part on the air-flow direction sensor detecting the direction of the turbulent air-flow that is influencing the plume to move in the path.

5. The system of claim 4, wherein:
   the system further comprises an air-flow speed sensor coupled to the movable orientation device; and
   the synchronized sensing operation further comprises:
      detecting, using the air-flow speed sensor, a speed of the turbulent air-flow that is influencing the plume to move in the path; and
      generating, using the air-flow speed sensor, air-flow speed data based at least in part on the air-flow speed sensor detecting the a speed of the turbulent air-flow that is influencing the plume to move in the path.

6. The system of claim 5, wherein:
   the system further comprises a transmission circuit configured to:
      receive the plume composition data, the air-flow direction data, and the air-flow speed data; and
      transmit the plume composition data, the air-flow direction data, and the air-flow speed data to a processor.

7. The system of claim 1 further comprising an air-flow speed sensor coupled to the movable orientation device.

8. The system of claim 7, wherein the synchronized sensing operation further comprises detecting, using the air-flow speed sensor, a speed of the turbulent air-flow that is influencing the plume to move in the path.

9. The system of claim 7, wherein the synchronized sensing operation further comprises positioning the turbulent air-flow speed sensor relative to the path such that the air-flow speed sensor is exposed to the turbulent air-flow.

10. The system of claim 7, wherein:
    the air-flow speed sensor comprises an air-flow guide element coupled to a pressure transducer;
    the synchronized sensing operation further comprises adjusting the position of the air-flow guide device relative to the path such that the air-flow guide element receives the plume and the turbulent air-flow that is influencing the plume to move along the path; and
    the air-flow guide device is configured to guide the turbulent air-flow to the pressure transducer.

* * * * *